United States Patent [19]

Wetzel et al.

[11] 3,932,537

[45] Jan. 13, 1976

[54] ALKYLATION OF PHENOLS

[75] Inventors: William H. Wetzel, Federal Way; Harold G. Nelson; Frederic J. Shelton, both of Tacoma, all of Wash.

[73] Assignee: Reichhold Chemicals, Inc., White Plains, N.Y.

[22] Filed: Aug. 9, 1974

[21] Appl. No.: 496,312

Related U.S. Application Data

[63] Continuation of Ser. No. 183,887, Sept. 9, 1971, abandoned.

[52] U.S. Cl.............................................. 260/624 C
[51] Int. Cl.².......................................... C07C 39/06
[58] Field of Search ........ 260/624 R, 624 C, 505 E, 260/505 C, 671; 252/182

[56] References Cited
UNITED STATES PATENTS

| | | | |
|---|---|---|---|
| 2,014,766 | 9/1935 | Ishom | 260/163 |
| 2,435,087 | 1/1948 | Luten et al. | 260/621 |
| 2,793,239 | 5/1957 | Toland et al. | 260/671 |
| 3,458,449 | 7/1969 | Mausner | 252/182 |

FOREIGN PATENTS OR APPLICATIONS 1,076,031   7/1967   United Kingdom............ 260/624 R Primary Examiner—James O. Thomas, Jr.
Assistant Examiner—W. B. Lone

[57] ABSTRACT

Improvement in a method for producing para-alkylated phenols comprising reacting (A) a phenol and (B) an alkylating agent in the presence of (C) an alkylation catalyst and resulting product. This improvement comprises using as (C) an aryl sulfonic acid selected from the class of highly acidic aryl sulfonic acids having a K value of at least $3.8 \times 10^{-3}$ including para-chlorobenzene sulfonic acid, 4,4'-diphenyldisulfonic acid, nitrobenzenesulfonic acids, 2,4,6-trinitrobenzenesulfonic acid and meta-benzenedisulfonic acid and also trifluoromethanesulfonic acid. These acid catalysts are also very effective in rearranging ortho and meta substituted phenols to parasubstituted phenols allowing use of normally discarded by-products as starting materials.

12 Claims, No Drawings

ALKYLATION OF PHENOLS

This is a continuation of application Ser. No. 183,887, filed Sept. 9, 1971 now abandoned. The invention relates to the production of selectively alkylated phenols namely para-alkylated phenols.

More specifically the invention relates to a method for producing para-alkylated phenols comprising reacting (A) a phenol and (B) an alkylating agent in the presence of (C) an alkylation catalyst and resulting product. More particularly this improvement comprises using as (C) an aryl sulfonic acid selected from the group including para-chlorobenzene sulfonic acid, 4,4'-diphenyldisulfonic acid, nitrobenzenesulfonic acids, 2,4,6-trinitrobenzenesulfonic acid and meta-benzenedisulfonic acid and also trifluoromethanesulfonic acid. These acid catalysts are also very effective in re-arranging ortho and meta substituted phenols to para-substituted phenols allowing use of normally discarded by-products as starting materials.

Alkylated phenols have been manufactured for many years and enjoy a wide variety of uses. They are used as intermediates in in the production of synthetic resins and varnishes, and when treated with ethylene oxide, surfactants are produced. Different processes have been suggested for the alkylation of phenols. They generally involve the reaction between a phenol and an alkylating agent in the presence of an acid catalyst. These acid catalysts include phosphoric acid, some arylmono-sulfonic and fluorosulfonic acids and anhydrous aluminum halides, zinc halides and boron trifluoride. Many of these catalysts, while effective in promoting alkylation, are not specific alkylation directors in that they do not appreciably favor alkylation at any one position. Therefore, they give a mixture at the end of the reaction which contains several products and generally not a majority of any one species. For this reason, boron trifluoride is the preferred catalyst because it produces para-alkylated products in excellent yields. In any event, no matter what catalyst is utilized, before a finished alkyl substituted phenol is obtained the crude reaction products must be processed in various ways to remove the catalyst such as neutralization, filtering to remove the resultant salt formed and distillation to obtain a pure product. Another disadvantage of boron trifluoride catalyst is that it is very corrosive to glass lined and stainless steel equipment.

According to a known process for producing para-alkylated phenols using boron trifluoride as the catalyst, the commonly used glass lined reactors and equipment suffer from heavy attack by the catalyst. This is due to the presence of minor amounts of water found in the reactants. Further, at the end of the reaction, prior to fractional distillation, the boron trifluoride catalyst must be neutralized with base and the resultant salt filtered and washed from the reaction mixture with the attendant cost in time, manpower and materials. Also all the washes must be carefully neutralized before being disposed of in the liquid waste system to eliminate any environmental pollution hazard. If the catalyst is not carefully removed before fractional distillation gaseous fluorides are released during the distillation step which will attack and corrode the apparatus. Also, it is found that if the finished product contains any catalyst residue it will cause degradation to paper and cardboard storage containers necessitating the use of more expensive types of storage containers.

It is, therefore, an object of this invention to produce para-alkylated phenols through the use of a powerful, highly selective catalyst.

It is also an object of this invention to product paraalkylated phenols through the use of a powerful, highly selective catalyst which does not attack or corrode glasslined and stainless steel reaction equipment.

Still another object of this invention is to produce paraalkylated phenols through the use of a powerful, highly selective catalyst which does not have to be removed after neutralization.

Yet another object of this invention is to produce paraalkylated phenols through the use of a powerful, high selective catalyst which allows distillation by-products to be re-cycled and rearranged to the desired product.

Still another object of this invention is to produce paraalkylated phenols through the use of a powerful, highly selective catalyst which lends itself to either batch wise or continuous production.

Still further objects and the entire scope of applicability of the present invention will become apparent from the detailed description give hereinafter; it should be understood, however, that the detailed description and specific examples while indicating preferred embodiments of the invention are given by way of illustration only, since various changes and modifications within the spirit and scope of the invention will become apparent to those skilled in the art from this detailed description.

It has now been found that these and other objects may be attained by using as the alkylation catalyst a highly acidic aryl sulfonic acid. These acids may be selected from a class of highly acidic aryl sulfonic acids including para-chlorobenzenesulfonic acid, 4,4'-diphenyldisulfonic acid, meta-nitrobenzenesulfonic acid, 2,4,6-trinitrobenzenesulfonic acid, para-nitrobenzensulfonic acid and meta-benzenedisulfonic acid and also trifluoromethanesulfonic acid. Through the use of these catalysts after the reaction has been completed, the catalyst is merely neutralized with any convenient base and then the reaction mass is purified by distillation. It is not necessary to remove the neutralized catalyst in any way as it ends up in the usual distillation bottoms which are discarded after each fractionation. There is no danger of accelerated corrosion of the equipment or distillation apparatus. Also, since these catalysts are very effective in re-arranging ortho and meta substituted phenols to the desired para-substituted compound the batch charge may include large amounts of recycled intermediate still fractions composed of ortho and meta substituted phenols which are normally discarded. Further, since the crude reaction mass does not have to be washed to remove the spent catalyst these are no large amounts of waste water to be released into the disposal system with the possible danger of evironmental pollution.

These catalysts are highly versatile in that they lend themselves to batchwise or continuous production. For example, the liquid reaction mixture may be passed through a coil which is heated to the desired temperature and whose dimensions are such that conversion has occurred by the time the mixture leaves the coil. The desireed neutralizing agent may be metered in and then the stream directed to the distillation apparatus.

Procedures for the alkylation of phenols with alcohols or olefins are well known to the art. For instance, the desired phenol may be placed into a suitable reaction apparatus along with a catalyst. The temperature is raised to about 125°C. and the alkylating agent is slowly added under the surface. After completion of the addition, the temperature is raised to about 150°C. for an hour to complete the reaction. The ratio of phenol to alkylating agent is generally in the range of about one mole of phenol per mole of alkylating agent.

Phenols which may be selectively alkylated in the para position through the use of the catalyst of this invention include phenol, cresol, resorcinol, ethyl, propyl, butyl, amyl, hexyl, heptyl, octyl, and nonyl phenols, as well as chlorophenols, bromophenols, and xylenol and the like and mixtures thereof. Other phenols may be selectively re-arranged to the para-position including ortho and meta-substituted phenols and di-alkyl substituted phenols such as ortho-tertiary butyl phenol and 2,4-ditertiarybutyl phenol and the like and mixtures thereof.

The alkylating agents may include any of these now employed in the art such as aliphatic, cyclic and aralkyl alcohols and olefins. Examples of suitable alkylating agents are:

| Alcohols | |
|---|---|
| Ethanol | Decanol |
| Propanol | Undecanol |
| Butanol | Dodecanol |
| Pentanol | Tetradecanol |
| Hexanol | Hexadecanol |
| Heptanol | Octadecanol |
| Octanol | Eicosanol |
| Nonanol | Phenyl-Ethanol |
| Olefins | |
| Ethylene | Undecene |
| Propene | Dodecene |
| Butene | Tetradecene |
| Pentene | Hexadecene |
| Hexene | Octadecene |
| Heptene | Eicosene |
| Octene | Triisobutylene |
| Nonene | Isobutylene |
| Decene | Diisobutylene | and the like, their isomers and mixtures thereof. The alkylating agent and the phenol are generally used in a mole ratio of about 1:1. However, as is well known in the art this may vary from less than 1:1 to 10:1 or more. But to obtain a majority of the paraalkylated product a ratio of about 0.9:1 is preferred.

Certain aromatic as well as certain alkyl sulfonic acids are suitable for use as catalyst under the practice of this invention. It has also been found that the effectiveness of these aromatic and alkyl sulfonic acids as selective para-alkylating agents appears to be directly related to their acid strength. For instance, para-toluenesulfonic acid is a weaker acid than meta-benzenedisulfonic acid. Because of the known electron withdrawing effect of one sulfonic acid group on the other, meta-benzenedisulfonic acid is a much stronger acid than para-toluenesulfonic acid. Thus, only a 34.0% yield of para-tertiarybutyl phenol is obtained when the relatively weak acidic para-toluenesulfonic acid is used as a catalyst in the butylation of phenol. However, when the stronger acid, meta-benzenedisulfonic acid is used as a catalyst in the same reaction the yield is 78% of the paratertiary-butylphenol product. (See Table I).

In order to define exactly what class of catalyst are suitable for the practice of instant invention a spectrophotometric method for measuring the relative acidities of the acids under study was used.

The effect of each acid, at 25°C, on a solution of a weakly basic dye, 4-chloro-2-nitroaniline was observed. This dye has a maximum absorbance at 415 (nm). A plot of absorbance (of the dye alone) vs. concentration (3-23 $\mu$ mole/ml) in glacial acetic acid solvent gave a linear Beer's Law plot. The strength of the acids under study was measured as a function of absorbance when added to a known concentration of the dye. The stronger the acid the more of the free basic dye was transformed to the conjugate acid and thus the lower the absorbance. The equation below represents this process.

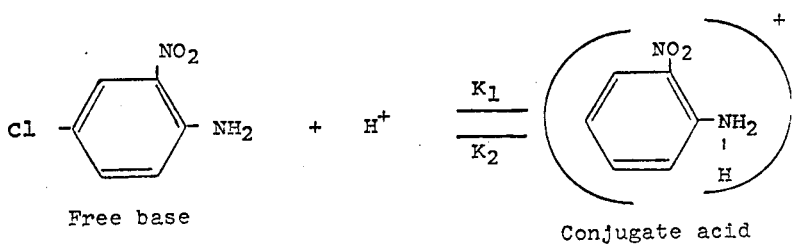

Free base    Conjugate acid or in general terms,

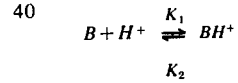

An equation, $$K = \left( \frac{\frac{[BH^+]}{[B]}}{HA} \right)^2$$

Where
K = the equilibrium expressing acidity of the acid studied.
[B] = concentration of the base (4-chloro-2-nitroanaline)
[BH$^+$] = concentration of the conjugate acid
[HA] = concentration of the undissociated catalyst acid has been derived, following the usual known spectrophotometric procedures for determining the equilibrium constants of the test catalyst acids and a direct relationship between acid strength and yield of para-tertiary-butyl phenol was obtained.

The derivation of the above equation for expressing relative acidities is shown below:

The dissociation of the acids studied is expressed by the equilibrium, $$HA = H^+ + A^- \qquad (1)$$

from where the equilibrium constant is derived, $$K_a = \frac{[H^+][A^-]}{[HA]} \quad (2)$$

where
$K_a$ = equilibrium constant of the acid studied.
$[H^+]$ = concentration of ionic hydrogen
$[A^-]$ = concentration of the anion
$[HA]$ = concentration of the undissociated acid The equilibrium involved in the reaction of the basic dye, 4-chloro-2-nitroanaline with the acids under study is expressed as, $$B + H^+ = BH^+ \quad (3)$$

and from this another equilibrium constant was obtained.

$$K_b = \frac{[BH^+]}{[B][H^+]} \quad (4)$$

Rearranging (4) above the following was obtained, $$[H^+] = \frac{[BH^+]}{[B]} \frac{1}{K_b} \quad (5)$$

where
$K_b$ = equilibrium constant of the basic dye, 4-chloro-2-nitroanaline
$[BH^+]$ = concentration of the conjugate acid
$[B]$ = concentration of the basic dye
$[H^+]$ = concentration of ionic hydrogen Since HA > $H^+$ or $A^-$ and assuming $H^+$ > B or $BH^+$. Then $H^+ = A^-$.

By substituting the value of $[H^+]$ from equation (5) above into equation (2) the following equation is formed, $$K_a = \left(\frac{[BH^+]}{[B]}\right)^2 \left(\frac{1}{K_b}\right)^2 \frac{1}{HA} \quad (6)$$

combining the constants $$K_a K_b^2 = \left(\frac{[BH^+]}{[B]}\right)^2 \frac{1}{HA}$$

or $$K = \frac{\left(\frac{[BH^+]}{[B]}\right)^2}{HA} \quad (7)$$

which is the expression used as a measure of acidity of the catalysts. The greater the value of K the greater is the acidity of the catalyst.

In Table I the direct relationship of K Values (equilibrium constants) of a number of acids with the yield of para-tertiarybutyl phenol in butylations of phenol using these acids is shown:

Table I

| Catalyst | Yield | K |
| --- | --- | --- |
| 2,5-dimethylbenzenesulfonic acid | 28 | 6.15 × 10⁻⁴ |
| para-toluenesulfonic acid | 34 | 8.96 × 10⁻⁴ |
| benzenesulfonic acid | 44 | 1.50 × 10⁻³ |
| para-chlorobenzenesulfonic acid | 62 | 3.80 × 10⁻³ |
| 4,4'-diphenyl disulfonic acid | 63 | 6.81 × 10⁻³ |
| meta-nitrobenzenesulfonic acid | 71 | 1.80 × 10⁻² |
| para-nitrobenzenesulfonic acid | 73 | 2.60 × 10⁻² |
| meta-benzenedisulfonic acid | 78 | 4.70 × 10⁻² |
| 2,4,6-trinitrobenzenesulfonic acid | 79 | 1.20 × 10⁻¹ |
| trifluoromethanesulfonic acid | 84 | 3.88 × 10⁻¹ |

The yields in Table I are expressed as analyzed weight percent of para-tertiary-butyl phenol in the crude reaction product.

The K values of some of the acids could not be obtained and included in the above table because of their insolubility in glacial acetic acid used as solvent for the spectrophotometric determinations.

Only the Lowry-Bronsted type acids were studied in Table I and defined as substances that give up a proton (hydrogen nucleus) to a base. The base used in this case of course is 4-chloro-2-nitroaniline. The Lewis acids such as boron trifluoride, zinc chloride and aluminum chloride contain no hydrogen and could not be properly included in the acidity study. They, however, were used along with the Lowry-bronsted acids simply to relate yields of para alkylated product obtained with then with that of the acids of our invention. See Table II.

It is thus seen, within the scope of our invention, that higher acid strengths of the catalyst acids give rise to higher yield of the para alkylated product. This relationship can be depicted graphically in FIG. I which shows that the yields increase rapidly with increasing K values at lower levels but tend to level out as the K value approaches values of 0.04 and above. The acid catalysts claimed in our invention are those having K value above and including 3.8 × 10⁻³ and thus comprise, among others that can fall in this range, para-chlorobenzenesulfonic acid, 4,4'-diphenyldisulfonic acid, ortho, meta and para-nitrobenzene sulfonic acids, meta-benzenedisulfonic acid, 2,4,6-trinitrobenzenesulfonic acid, 1,3,5-mesitylenedisulfonic acid, 2,2', 4,4'-diphenyltetrasulfonic acid, 1,4,5-naphalenetrisulfonic acid, 2,4-dichlorobenzene disulfonic acid, ortho-dischlorobenzenedisulfonic acid, 2,6-meta-xylene-disulfonic acid, 2,7-fluorenedisulfonic acid, 1,3,5-benzenetrisulfonic acid and trifluromethane sulfonic acid and the like. However the preferred catalyst may include para-chlorobenzenesulfonic acid, 4,4'-diphenyldisulfonic acid, meta-and para-nitrobenzenesulfonic acids, 2,4,6-trinitrobenzenesulfonic acid, meta-benzenedisulfonic acid and trifluoromethanesulfonic acid with meta-benzenedisulfonic being favored because of the excellent results obtained therefrom.

The amount of catalyst used is based upon the weight of phenol used and may range from about 0.05% to about 20% by weight. However, the preferred range is from about 0.1% to about 2% by weight based upon the amount of phenol used.

The temperature for the reaction may range from about 10° to about 185°C. although the reaction may be run at higher temperatures when pressure is applied to the system. Temperatures ranging from about 90° to about 170°C. are preferred.

In a typical practice of this invention 564 grams of phenol were charged into a reaction flask equipped with stirrer, heating mantle, sparge for adding alkylating agent and reflux condenser along with 5 grams of meta-benzenedisulfonic acid. The temperature was raised to 120°C. with stirring and 315 grams of isobutylene were sparged in at the rate of about 60 grams per hour. After the addition was completed, the batch was heated up to 150°C. and held at this temperature for an additional hour. The yield of para-tertiarybutyl phenol in this mixture was 92% based upon isobutylene. Then the temperature was reduced to about 100°C. and aqueous sodium hydroxide was slowly added. After the batch was neutralized the flask was arranged for vacuum distillation and purified para-tertiarybutyl phenol was distilled off under vacuum.

This invention will now be more specifically described in and by the following examples which are given for the purpose of illustration only and are not meant to be limiting in any manner except as described in the appended claims.

EXAMPLE I

Into a reaction flask equipped with stirrer, heating mantle, sparge for adding alkylating agent, and reflux condenser were charged 564 grams of phenol and 5 grams of para-nitrobenzenesulfonic acid. The temperature was raised to 120°C. with stirring and then 315 grams of isobutylene were sparged in at the rate of about 60 grams per hour. After the isobutylene addition was completed, the batch was heated to 150°C. for 1 hour. Upon cooling, the crude reaction mixture contained 73% para-tertiary-butyl phenol.

EXAMPLE II

Example I was repeated except that no catalyst was used. The crude reaction mixture contained 92% phenol and only 3.2% paratertiary-butyl phenol.

EXAMPLE III

Example I was repeated except that 20 grams of meta-benzene disulfonic acid was used as the catalyst. The reaction temperature was held at 42°C. during part of the addition of the isobutylene and then lowered to 13°C. for the remainder of the addition and then raised to 150°C. for 1 hour to complete the reaction. The crude reaction mixture contained 78.7% para-tertiarybutyl phenol.

EXAMPLE IV

Example III repeated exactly that the reaction temperature was 185°C. for the entire reaction. The crude reaction mixture contained 74% para-tertiarybutyl phenol.

EXAMPLE V

Five hundred and sixty-four grams (6 moles) of phenol containing 5 grams of trifluoromethanesulfonic acid catalyst was stirred at 90°C. and butylated with isobutylene to a degree of 0.92. The batch was then heated to 120°C. for one hour with stirring. Analysis of the crude product gave 84% weight para-tertiary-butyl phenol.

EXAMPLE VI

Two grams of ortho-tertiary-butyl phenol was mixed with 1% of meta-benzenedisulfonic acid and heated in a test tube for 1.5 hours with occasional stirring at 150°C. Analysis gave 84.0% para-tertiary-butyl phenol; the remaining components consisted of its isomers.

EXAMPLE VII

Thus, to 2.06 grams of 2,4-ditertiary-butyl phenol was added 0.94 grams of phenol. Then 1% of meta-benzenedisulfonic acid was stirred in with warming and the final mixture was heated to 150°C. for 1.5 hours. Analysis gave 81.2% para-tertiary-butyl phenol. The remaining components were its isomers.

EXAMPLE VIII

The following catalysts were used to butylate phenol similarly to the procedure in Example I.

| Acid Catalyst | Percent Yield Para-Tertiary-Butyl Phenol |
| --- | --- |
| 1,4-5-naphthalenetrisulfonic acid | 64.0 |
| para-chlorobenzenesulfonic acid | 62.0 |
| 4,4'-diphenyldisulfonic acid | 63.0 |
| meta-nitrobenzenesulfonic acid | 71.0 |
| 2,4,6-trinitrobenzenesulfonic acid | 79.0 |
| 1,3,5-mesitylenedisulfonic acid | 72.0 |
| 2,2',4,4'-diphenyl tetrasulfonic acid | 75.9 |
| 2,4-dichlorobenzenedisulfonic acid | 71.1 |
| ortho-dichlorobenzenedisulfonic acid | 80.1 |
| 4,6-meta-xylenedisulfonic acid | 72.7 |
| 2,7-fluorenedisulfonic acid | 74.9 |
| 1,3,5-benzenetrisulfonic acid | 79.6 |

TABLE II

Comparison of Effectiveness of m-Benzenedisulfonic Acid Catalyst

| Experiment | | Reaction Time °C | Catalyst | Weight Crude Product Grams | Phenol % | Analysis p-tertiary butyl phenol,% | Analysis o-tertiary butyl phenol,% | 2,4-di tertiary butyl phenol,% |
| --- | --- | --- | --- | --- | --- | --- | --- | --- |
| 1 | A | 120 | p-toluene- | 844 | 23.3 | 23.4 | 25.4 | 26.9 |
| | B | 150 | sulfonic acid | | 22.5 | 34.5 | 16.1 | 21.0 |
| 2 | A | 120 | m-xylenesulfonic | 864 | 25.3 | 11.4 | 31.7 | 30.7 |
| | B | 150 | Acid | | 20.2 | 36.5 | 18.3 | 24.1 |
| 3 | A | 120 | m-benzene-disulfonic | 860 | 16.7 | 67.7 | 4.2 | 10.4 |
| | B | 150 | acid | | 14.1 | 78.2 | 2.0 | 4.9 |
| 4 | A | 120 | sulfonic acid | 855 | 18.1 | 34.6 | 17.3 | 28.0 |
| | B | 150 | | | 11.1 | 69.3 | 6.5 | 12.4 |
| 5 | A | 120 | Zinc Chloride | | 27.5 | 23.6 | 13.2 | 37.6 |
| | B | 150 | Acetic Acid Mixture | 844 | 22.6 | 28.2 | 13.2 | 35.2 |
| 6 | A | 120 | Phosphoric | 669 | 64.5 | 8.4 | 21.0 | 5.0 |
| | B | 150 | Acid | | 62.2 | 5.8 | 23.8 | 7.0 |
| 7 | A | 120 | Aluminum | 696 | 57.4 | 24.2 | 11.5 | 6.6 |
| | B | 150 | Chloride | | 5.5 | 22.2 | 12.5 | 10.0 |
| 8 | A | 120 | 2,5-dimethyl- | | 25.9 | 14.3 | 30.5 | 28.3 |
| | B | 150 | benzenesulfonic Acid | 859 | 26.0 | 27.7 | 21.8 | 23.8 |
| 9 | A | 120 | borontriflouride | 850 | 15.2 | 68.7 | 5.0 | 11.5 |
| | B | 140 | | | 10.6 | 78.6 | 2.2 | 8.6 |

EXAMPLE IX

A reaction flask was set up according to Example I. Then 546 grams phenol and 5 grams of meta-benzenedisulfonic acid were added and the whole heated to 100°C. with stirring. At this point 350 grams of isobutylene were added over a period of 30 minutes. The temperature was then raised to 150°C. for 1 hours. The crude reaction contained 78% para-tertiarybutyl phenol.

EXAMPLE X

To a reaction set up as described in Example I was charged 647 grams of ortho-cresol and 5 grams of meta-benzenedisulfonic acid and then heated with stirring to 120°C. Then 300 grams of isobutylene was added over a period of 5 hours and 27 minutes. At this point, the temperature was heated at 150°C. for 1 hour and 15 minutes. The crude product contained 79% para-tertiarybutyl ortho-cresol.

EXAMPLE XI

This experiment compares the alkylating power of metabenzenedisulfonic with other previously noted literature catalysts used in alkylation reactions. The procedure as outlined in Example I was followed except that a sample was removed for analysis before the temperature was raised to 150°C. (A) and again when the reaction was terminated (B). These results are shown in the following table, Table II.

EXAMPLE XII

The effectiveness of meta-benzene disulfonic acid as a catalyst for alkylation of phenol with olefins other than isobutylene is demonstrated in this example where isoamylene was used. The same equipment was employed as in Example I, except that instead of using a gas sparger to introduce the olefin, a separatory funnel was subtituted to introduce the liquid isoamylene dropwise under the stirred phenol. Thus 100 grams of phenol was mixed with 0.8 grams of meta-benzene disulfonic acid and the whole heated to 120°C with stirring. Then 75 grams of 2-methyl-2-butene (isoamylene) was added in a period of 30 minutes with stirring. It was then heated to 150°C and held there with continued stirring for one hour. The crude brown product weighed 170 grams which analyzed as 87% para-tertiary amyl phenol.

What is claimed is:

1. In a process for producing para-alkylated phenols comprising reacting at a temperature ranging from about 10° to about 185°C (A) a phenol which is at least one member selected from the group consisting ortho-tertiarybutyl phenol ertho-tertiarybutyl phenol and 2,4-ditertiarybutyl phenol and (B) an alkylating agent consisting of aliphatic olefins having from 20 to about 20 carbon atoms in the presence of (C) from about 0.05% to about 20% by weight based upon the amount of (A) used of an alkylation catalyst; the improvement consisting of using as the alkylation catalyst (C) an aryl sulfonic acid which is at least one member selected from the class of highly acidic aryl sulfonic acids having a K value of at least $3.8 \times 10^{-3}$.

2. The process as set forth in claim 1 which is carried out in the absence of water.

3. In a process for producing para-alkylated phenols comprising reacting at a temperature ranging from about 10° to about 185°C (A) a phenol which is at least one member selected from the group consisting of phenol ortho-tertiarybutyl phenol and 2,4-ditertiarybutyl phenol and (B) an alkylating agent consisting of aliphatic olefins having carbon to carbon linkages and from 2 to about 20 carbon atoms in the presence of (C) from about 0.5% to about 20% by weight based upon the amount of (A) used of an alkylation catalyst; the improvement consisting of using as the alkylation catalyst (C) an aryl sulfonic acid selected from the group consisting of meta-benzenedisulfonic acid, 2,4,6-trinitrobenzenesulfonic acid and trifluoromethane sulfonic acid.

4. In a process for producing para-alkylated phenols according to claim 3 comprising reacting at a temperature ranging from about 10° to about 185°C (A) a phenol which is at least one member selected from the group consisting of phenol ortho-tertiarybutyl phenol and 2,4-ditertiarybutyl phenol and (B) an alkylating agent consisting of aliphatic olefins having carbon to carbon linkages and from 2 to about 20 carbon atoms in the presence of (C) from about 0.05% to about 20% by weight based upon the amount of (A) used of an alkylation catalyst; the improvement consisting of using as the alkylation catalyst (C) meta-benzenedisulfonic acid.

5. In a process for producing para-alkylated phenols according to claim 3 comprising reacting at a temperature ranging from about 10° to about 185°C (A) a phenol which is at least one member selected from the group consisting of phenol ortho-tertiarybutyl phenol and 2,4-ditertiaybutyl phenol and (B) an alkylating agent consisting of aliphatic olefins having carbon to carbon linkages and from about 2 to about 20 carbon atoms in the presence of (C) from about 0.05% to about 20% by weight based upon the amount of (A) used of an alkylation catalyst; the improvement consisting of using as the alkylation catalyst (C) 4,4'-diphenyldisulfonic acid.

6. In a process for producing para-alkylated phenols according to claim 3 comprising reacting at a temperature ranging from about 10° to about 185°C (A) a phenol which is at least one member selected from the group consisting of phenol ortho-tertiarybutyl phenol and 2,4-ditertiarybutyl phenol and (B) an alkylating agent consisting of aliphatic olefins having carbon to carbon linkages and from 2 to about 20 carbon atoms in the presence of (C) from about 0.05% to about 20% by weight based upon the amount of (A) used of an alkylation catalyst; the improvement consisting of using the alkylation catalyst (C) trifluoromethane sulfonic acid.

7. The process as set forth in claim 3 which is carried out in the absence of water.

8. In a process for producing para-tertiary-butyl phenol comprising reacting at a temperature ranging from about 10° to about 185°C (A) a phenol which is at least one member selected from the group consisting of phenol, ortho-tertiary butyl phenol and 2,4-ditertiarybutyl phenol and (B) isobutylene of (C) from about 0.05% to about 20% by weight based upon the amount of (A) used of an alkylation catalyst; the improvement consisting of using as the alkylation catalyst (C) an aryl sulfonic acid which is at least one member selected from the group consisting of meta-benzenedisulfonic acid, 2,4,6-trinitrobenzenesulfonic acid and trifluoromethane sulfonic acid.

9. In a process for producing para-tertiary-butyl phenol according to claim 8 comprising reacting at a temperature ranging from about 10° to about 185°C (A) a phenol which is at least one member selected from the group consisting of phenol, ortho-tertiarybutyl phenol and 2,4-ditertiarybutyl phenol and (B) isobutylene in the presence of (C) from about 0.05% to about 20% by weight based upon the amount of (A) used of an alkylation catalyst; the improvement consisting of using as the alkylation catalyst (C) meta-benzenedisulfonic acid.

10. In a process for producing para-tertiary-butyl phenol according to claim 8 comprising reacting at a temperature ranging from about 10° to about 185°C (A) a phenol which is at least one member selected from the group consisting of phenol, ortho-tertiarybutyl pehnol and 2,4-ditertiarybutyl phenol and (B) isobutylene in the presence of (C) from about 0.05% to about 20% by weight based upon the amount of (A) used of an alkylation catalyst; the improvement consisting of using as the alkylation catalyst (C) 2,4,6-trinitrobenzenesulfonic acid.

11. In a process for producing para-tertiary-butyl phenol according to claim 8 comprising reacting at a temperature ranging from about 10° to about 185°C (A) a phenol which is at least one member selected from the group consisting of phenol, ortho-tertiarybutyl phenol and 2,4-ditertiarybutyl phenol and (B) isobutylene in the presence of (C) from about 0.05% to about 20% by weight based upon the amont of (A) used of an alkylation catalyst; the improvement consisting of using as the alkylation catalyst (C) trifluoromethane sulfonic acid.

12. The process as set forth in claim 8 which is carried out in the absence of water.

* * * * *

UNITED STATES PATENT OFFICE
CERTIFICATE OF CORRECTION

Patent No. 3,932,537    Dated Jan. 13, 1976

Inventor(s) William H. Wetzel; Harold G. Nelson; Frederic J. Shelton

It is certified that error appears in the above-identified patent and that said Letters Patent are hereby corrected as shown below:

Column 4, equation under line 45 should read as follows:

$$K = \frac{\left(\frac{[BH^+]}{[B]}\right)^2}{HA}$$

Column 4, line 44 should read as follows:

--An equation has been derived, following the usual known spectrophotometric procedures for determining the equilibrium constants of the test catalyst acids and a direct relationship between acid strength and yield of para-tertiary-butyl phenol was obtained.

Cancel lines "57-61", see insert 2 above.

Column 5, equation between lines 45 and 50 should read:

$$K = \frac{\left(\frac{[BH^+]}{[B]}\right)^2}{HA}$$

UNITED STATES PATENT OFFICE
CERTIFICATE OF CORRECTION

Patent No. 3,932,537             Dated Jan. 13, 1976

Inventor(s) William H. Wetzel; Harold G. Nelson; Frederic J. Shelton

It is certified that error appears in the above-identified patent and that said Letters Patent are hereby corrected as shown below:

Column 6, line 23, cancel "Fig. I" and substitute --the accompanying drawing--.

Note: Transfer drawing submitted with parent application, Ser. No. 183,887 but omitted in Ser. No. 496,312, print enclosed.

In Table II, columns 7 and 8, the description of "column" 3 in the table reads "Reaction time °C"; it should read --Reaction temperature, °C--.

In column 7, line 65, the word --except-- should be inserted between "exactly" and "that".

Column 9, lines 53 and 54, should read --one member selected from the group consisting of phenol, ortho-tertiarybutyl phenol and -- instead of "---one member selected from the group consisting ortho-tertiarybutyl phenol ertho-tertiarybutyl phenol and---".

Column 9, line 56, "20" should be changed to --2--.

UNITED STATES PATENT OFFICE
CERTIFICATE OF CORRECTION

Patent No. 3,932,537                    Dated Jan. 13, 1976

Inventor(s) William H. Wetzel; Harold G. Nelson; Frederic J. Shelton

It is certified that error appears in the above-identified patent and that said Letters Patent are hereby corrected as shown below:

Column 10, line 2, insert comma --,-- between "phenol" and "ortho".

Column 10, line 6, the "0.5%" should be changed to --0.05%--.

Column 10, line 17, should have a comma --,-- between "phenol" and "ortho".

Column 10, line 30, should have a comma --,-- between "phenol" and "ortho".

Column 10, line 31, the chemical "name" "2,4-ditertiay-butyl phenol" should be spelled --2,4-ditertiarybutyl phenol--.

Column 10, line 43, should have a comma --,-- between "phenol" and "ortho".

Signed and Sealed this

Fifteenth Day of February 1977

[SEAL]

Attest:

RUTH C. MASON
Attesting Officer

C. MARSHALL DANN
Commissioner of Patents and Trademarks